US008605266B2

(12) United States Patent
Tezuka et al.

(10) Patent No.: US 8,605,266 B2
(45) Date of Patent: *Dec. 10, 2013

(54) COMPONENT MEASUREMENT APPARATUS WITH VARIABLE FOCUSING AND SATBLE LIGHT SOURCE OUTPUT

(75) Inventors: Shin-ichiro Tezuka, Musashino (JP); Hitoshi Hara, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 371 days.

This patent is subject to a terminal disclaimer.

(21) Appl. No.: 13/041,097

(22) Filed: Mar. 4, 2011

(65) Prior Publication Data
US 2011/0216309 A1   Sep. 8, 2011

(30) Foreign Application Priority Data
Mar. 4, 2010   (JP) .................................. 2010-047719

(51) Int. Cl.
*G01N 33/48* (2006.01)
*G02B 7/04* (2006.01)

(52) U.S. Cl.
USPC ...................... 356/39; 250/201.3; 250/227.26

(58) Field of Classification Search
USPC ................. 356/39, 432–44, 445; 372/29.011; 250/201.3, 227.26
See application file for complete search history.

(56) References Cited

U.S. PATENT DOCUMENTS

| 5,132,526 | A * | 7/1992 | Iwasaki | 250/201.3 |
| 2003/0151742 | A1 * | 8/2003 | Silvermintz et al. | 356/318 |
| 2008/0247743 | A1 * | 10/2008 | Liang et al. | 396/175 |
| 2009/0147809 | A1 * | 6/2009 | Yamada | 372/29.011 |

FOREIGN PATENT DOCUMENTS

JP    2008-301944 A    12/2008

OTHER PUBLICATIONS

Miyauchi, Yuki et al "Development of Noninvasive Blood Glucose Measuring Instrument by Near-Infrared Confocal Optical System," 8th Symposium of the Japanese Society for Medical and Biological Engineering, Apr. 23, 2009, p. 7-8.
Miyauchi, Yuki et al "Noninvasive measurement of blood glucose level with use of near-infrared confocal laser," 48th Meeting of the Japan Society for Medical and Biological Engineers, Apr. 2009, p. 148.
Miyauchi, Yuki et al "Non-invasive method for measuring blood sugar level by confocal optical system with near-infrared laser" Symposium of Medicine and Biology 2009, Sep. 2009, p. 387.

* cited by examiner

*Primary Examiner* — Tara S Pajoohi Gomez
*Assistant Examiner* — Michael P Lapage
(74) *Attorney, Agent, or Firm* — Westerman, Hattori, Daniels & Adrian, LLP (57) ABSTRACT

A component measurement apparatus includes a confocal optical system including a laser emitting laser light, a collimating lens collimating the laser light emitted from the laser, an objective lens condensing the collimated light having exited the collimating lens in order to illuminate internal tissue of an object of measurement, a half mirror redirecting reflected light reflected by the internal tissue of the object of measurement and refracted by the objective lens, a pin hole through which the reflected light redirected by the half mirror passes, and a light-receiving element receiving the reflected light having passed through the pin hole. The component measurement apparatus also includes a data analyzer section measuring a component of the object of measurement in accordance with data output from the light-receiving element. In the component measurement the apparatus, a focal position of the objective lens is adjustable along an optical axis.

11 Claims, 9 Drawing Sheets

COMPONENT MEASUREMENT APPARATUS WITH VARIABLE FOCUSING AND SATBLE LIGHT SOURCE OUTPUT

BACKGROUND OF THE INVENTION

1. Field of the Invention

The present disclosure relates to component measurement apparatuses. A particular aspect of the present disclosure relates to improvement of a component measurement apparatus that measures concentrations and so forth of components using laser light.

2. Description of the Related Art

To date, in order to measure a concentration of a component such as a blood glucose level, in many cases human blood is collected with a syringe or by pricking a finger tip or an earlobe in order to measure a blood glucose concentration or so forth.

In general, a blood glucose level significantly changes depending on measurement conditions such as whether a subject has recently had a meal or not or whether a subject performs exercise or not just before the blood sample is collected. Thus, frequent measurement is required in order to obtain correct blood glucose data. However, with a related art method in which a direct analysis is performed on a human blood sample that is collected every time such an analysis is performed, there is a problem in that the subject experiences a significant physical pain.

The assignee previously filed a patent application for a living body component measurement apparatus using a confocal optical system (see Japanese Unexamined Patent Application Publication No. 2008-301944). With this apparatus, a living body is illuminated by laser light, and the reflected light from the living body is detected. In accordance with a degree of laser light absorption by the living body (absorbance), the apparatus measures a concentration or so forth of a target component (for example, glucose in blood) without an invasive procedure for collecting a blood sample performed in the related art method.

Figure 9:
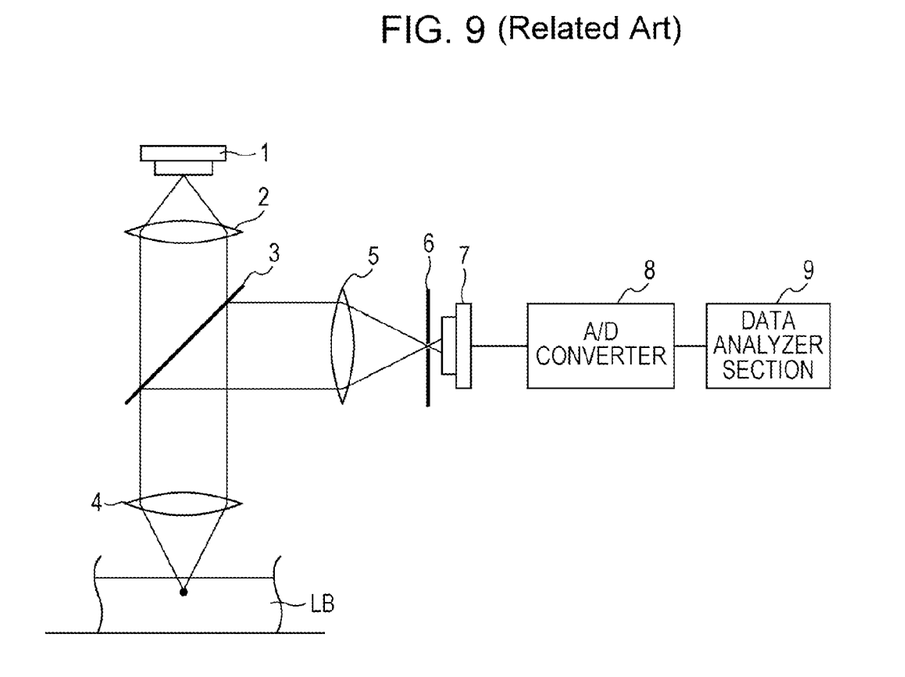
FIG. 9 is a block diagram illustrating an example of a related art living body component measurement apparatus.

FIG. 9 is a block diagram illustrating the living body component measurement apparatus disclosed in the above document. In FIG. 9, laser light emitted from a laser diode 1 is shaped into collimated light by a collimating lens 2 and strikes a half mirror 3 that is disposed so as to be inclined at about 45 degrees relative to the optical axis of the collimating lens 2. The laser diode 1 used here is, for example, a variable wavelength laser that can emit laser light in a wavelength region of 1600 nm to 1700 nm. Glucose absorbs a comparatively large amount of light in that wavelength region.

The collimated light having been transmitted through the half mirror 3 is condensed by an objective lens 4 and illuminates internal tissue of the living body LB. The laser light reflected by the internal tissue of the living body LB again strikes the objective lens 4, is shaped into collimated right, strikes the half mirror 3, and is redirected so as to be reflected at an angle of about 90 degrees.

The laser light, which has been reflected and redirected by the half mirror 3, is condensed by a lens 5 and strikes a pin hole 6. The laser light having passed through the pin hole 6 strikes a light-receiving element 7 and is converted into an electrical signal.

The light-receiving element 7 converts the received laser light into an electrical signal, the strength and the magnitude of which increase or decrease in accordance with the light amount of the received laser light, and sends the resultant signal to an analog to digital (A/D) converter 8. The A/D converter 8 converts the electrical signal received from the light-receiving element 7 into digital data, and sends the digital data to a data analyzer section 9.

When the living body LB is illuminated with laser light beams having two or more wavelengths different from each other, the data analyzer section 9 performs a quantitative analysis of a component of the living body LB in accordance with a plurality of electrical signals having been converted by and output from the light-receiving element 7.

Specifically, in order to quantitatively determine a blood glucose level, that is, a concentration of glucose in blood, a calibration curve that relates glucose concentrations having been measured to laser light absorbance values has been memorized in the data analyzer section 9 in advance. The data analyzer section 9 quantitatively determines a concentration of blood glucose of the living body LB in accordance with the calibration curve.

However, in the above-described related art living body component measurement apparatus, the positional relationship between the objective lens 4 and the living body LB, which is an object of measurement, is fixed. As a result, there is a problem in that a measurement position along a depth direction of the object of measurement cannot be easily changed.

SUMMARY OF THE INVENTION

An object of the present disclosure is to achieve a component measurement apparatus with which measurement data from a desired measurement position along the depth direction of the object of measurement can be adequately obtained.

To achieve such a task, a component measurement apparatus according to an aspect of the present disclosure includes a confocal optical system that includes a laser that emits laser light, a collimating lens that shapes the laser light emitted from the laser into collimated light, an objective lens that condenses the collimated light having exited the collimating lens in order to illuminate internal tissue of an object of measurement, a half mirror that redirects reflected light reflected by the internal tissue of the object of measurement and refracted by the objective lens, a pin hole through which the reflected light redirected by the half mirror passes, and a light-receiving element that receives the reflected light having passed through the pin hole. The component measurement apparatus also includes a data analyzer section that measures a component of the object of measurement in accordance with data output from the light-receiving element, in which a focal position of the objective lens is adjustable in an optical axis direction.

Preferably, the laser is a variable wavelength light source in the component measurement apparatus.

Preferably, the objective lens is provided so as to be movable in the optical axis direction in the component measurement apparatus.

Preferably, a motion drive mechanism that moves the confocal optical system and the object of measurement relatively to each other in three dimensions is included in the component measurement apparatus.

Preferably, a the component of the object of measurement is glucose in blood, and the data analyzer section quantitatively determines a concentration of the glucose by measuring absorbance of the glucose in the internal tissue of the object of measurement in accordance with the data output from the light-receiving element and quantitatively determines a blood glucose level in the component measurement apparatus.

Preferably, the objective lens is a varifocal lens in the component measurement apparatus.

Preferably, the component measurement apparatus further includes an optical fiber used to illuminate a surface of the object of measurement with the output light of the laser, a second light-receiving element that detects the reflected light reflected by the surface of the object of measurement due to illumination using the optical fiber, and a laser driver circuit that drives the laser so as to maintain the output light intensity of the laser at a certain value in accordance with a detection signal of the second light-receiving element.

Preferably, the data analyzer section measures the component of the object of measurement in accordance with normalized data obtained by dividing a detection signal of the light-receiving element that detects the reflected light reflected by the internal tissue of the object of measurement through the confocal optical system by the detection signal of the second light-receiving element in the component measurement apparatus. The data analyzer can be a computer, or it can be a logic-containing circuit board or the like.

Preferably, the laser includes a third light-receiving element therein that monitors the output light thereof, and the laser driver circuit drives the laser in accordance with at least one of the detection signal of the second light-receiving element and a detection signal of the third light-receiving element so as to maintain the output light intensity of the laser at a certain value in the component measurement apparatus.

Preferably, the laser includes a third light-receiving element therein that monitors the output light thereof, and the data analyzer section measures the component of the object of measurement in accordance with normalized data obtained by dividing a detection signal of the light-receiving element that detects the reflected light reflected by the internal tissue of the object of measurement through the confocal optical system by at least one of the detection signal of the second light-receiving element and a detection signal of the third light-receiving element in the component measurement apparatus.

Preferably, the laser includes a third light-receiving element therein that monitors the output light thereof, and the data analyzer section measures the component of the object of measurement in accordance with data obtained by linear combination of a first normalized signal and a second normalized signal. The first normalized signal is obtained by dividing a detection signal of the light-receiving element that detects the reflected light reflected by the internal tissue of the object of measurement through the confocal optical system by the detection signal of the second light-receiving element. The second normalized signal is obtained by dividing the detection signal of the light-receiving element that detects the reflected light reflected by the internal tissue of the object of measurement through the confocal optical system by a detection signal of the third light-receiving element in the component measurement.

Preferably, the component measurement apparatus further includes a fourth light-receiving element that detects the reflected light reflected by the half mirror that is provided in an optical path of the laser light, and the laser driver circuit drives the laser in accordance with at least one of the detection signal of the second light-receiving element, the detection signal of the third light-receiving element, and a detection signal of the fourth light-receiving element so as to maintain the output light intensity of the laser at a certain value.

Preferably, the data analyzer section measures the component of the object of measurement in accordance with normalized data obtained by dividing the detection signal of the light-receiving element that detects the reflected light reflected by the internal tissue of the object of measurement through the confocal optical system by at least one of the detection signal of the second light-receiving element, the detection signal of the third light-receiving element, the detection signal of the fourth light-receiving element in the component measurement apparatus.

Preferably, the data analyzer section measures the component of the object of measurement in accordance with data obtained by linear combination of normalized signals obtained by dividing the detection signal of the light-receiving element that detects the reflected light reflected by the internal tissue of the object of measurement through the confocal optical system by each of the detection signals of the second, third, and fourth light-receiving elements in the component measurement apparatus.

With the structure described as above, a component measurement apparatus can adequately obtain measurement data from a desired measurement position along a depth direction of the object of measurement.

DESCRIPTION OF THE PREFERRED EMBODIMENTS

Figure 1:
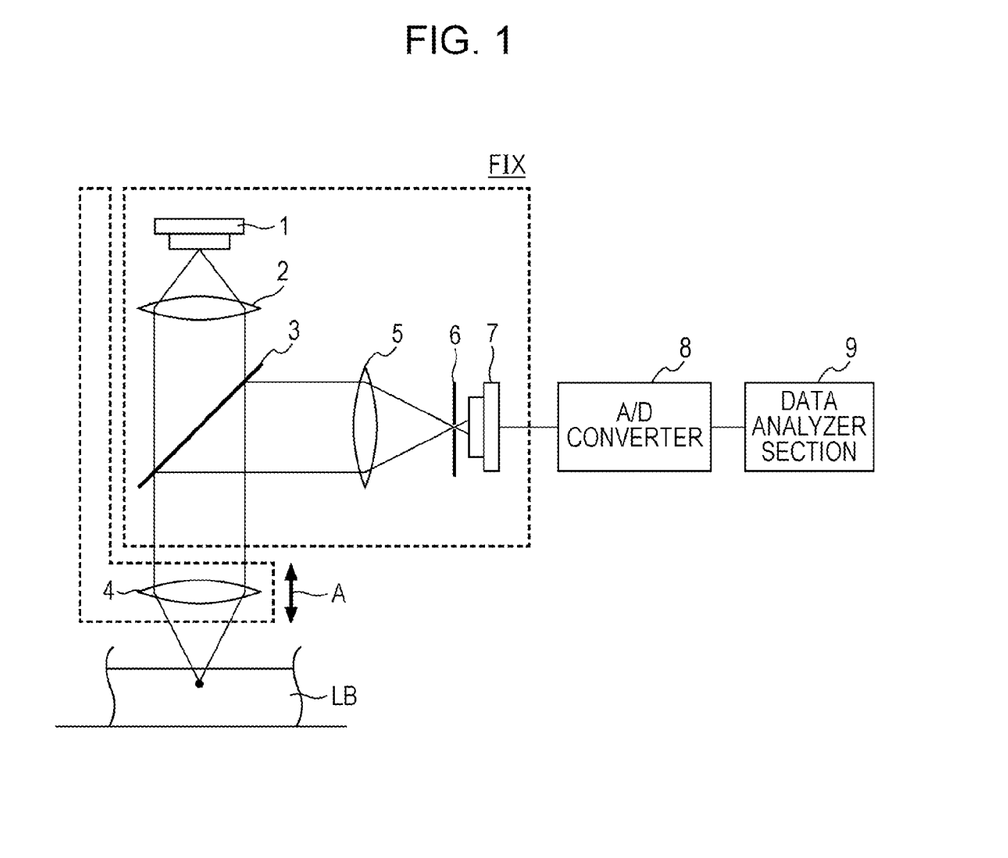
FIG. 1 is a block diagram illustrating an embodiment according to the present disclosure.

Embodiments according to the present disclosure will be described below in detail with reference to the drawings. FIG. 1 is a block diagram illustrating an embodiment according to the present disclosure. Components similar to those in FIG. 9 are denoted by similar signs. A difference between an apparatus illustrated in FIG. 1 and the apparatus illustrated in FIG. 9 is that the apparatus illustrated in FIG. 1 is provided with an objective lens 4, which is part of a confocal optical system of the apparatus, and which is disposed so as to be movable along the optical axis A of the objective lens 4.

Referring to FIG. 1, the objective lens 4 is included in the confocal optical system that, in addition to the objective lens 4, includes a laser diode 1, a collimating lens 2, a half mirror 3, a lens 5, a pin hole 6, and a light-receiving element 7. The laser diode 1 emits laser light. The collimating lens 2 shapes the laser light emitted from the laser diode 1 into collimated light. The half mirror 3 transmits the collimated light having exited the collimating lens 2 and redirects reflected light reflected by internal tissue of a living body LB, which is an object of measurement, and refracted by the objective lens 4. The lens 5 condenses the reflected light redirected by the half mirror 3. The pin hole 6 transmits the reflected light condensed by the lens 5 therethrough. The light-receiving element 7 receives the reflected light having passed through the pin hole 6. A fixed portion FIX, which is the confocal optical system other than the objective lens 4, is contained in and secured to a casing (not shown) such that the objective lens 4 is movable along the optical axis A thereof relative to the fixed portion FIX.

A movement mechanism of the objective lens 4 described as above includes a varying mechanism including a piezo actuator using a piezoelectric element, a movement mechanism using gears, and so forth. The movement mechanism actually changes the distance between the half mirror 3 and the objective lens 4.

By moving the objective lens 4 along the direction of the optical axis A thereof as described above, a measurement position in the living body LB can be desirably changed along the depth direction.

Figure 2:
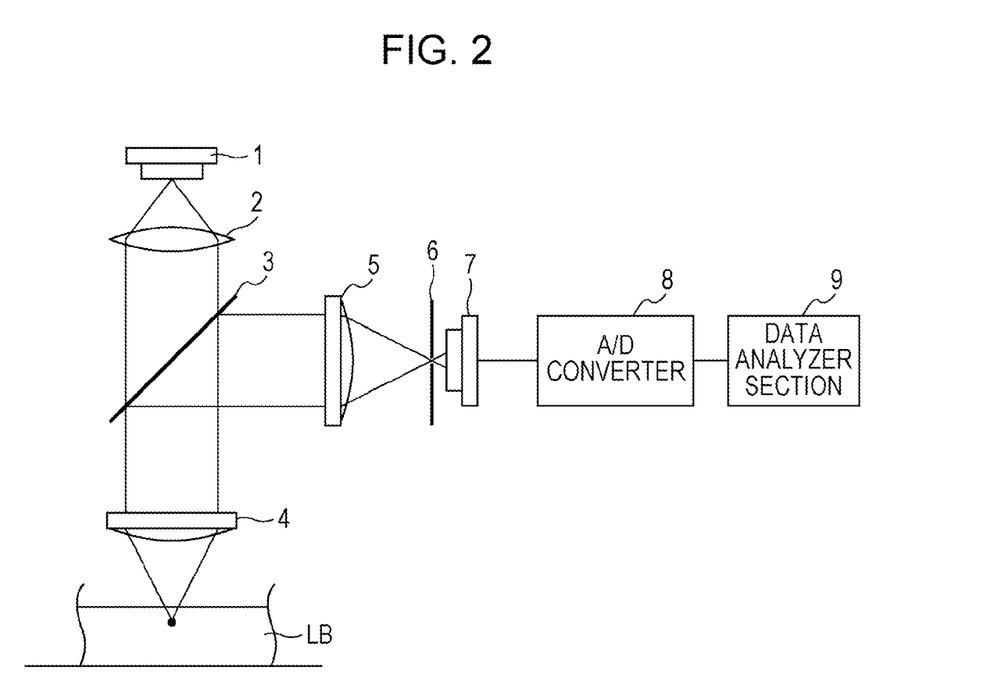
FIG. 2 is a block diagram illustrating another embodiment according to the present disclosure.

FIG. 2 is a block diagram illustrating another embodiment according to the present disclosure. In the embodiment illustrated in FIG. 2, a varifocal lenses are used as the objective lens 4 and the lens 5 that condenses the reflected light. As a varifocal lens, a liquid crystal lens is used. The liquid crystal lens has a structure in which, for example, a space formed to have a lens-like shape is filled with liquid crystals encapsulated therein and the refractive index of the liquid crystals is in effect changed by adjusting an applied voltage. With the liquid crystal lens, the focal distance can change in accordance with changes in the refractive index of the material despite the shape of the lens being unchanged.

By the use of such a varifocal lens as the objective lens 4, a measurement position in the depth direction in the tissue of the living body LB can be desirably set by simply adjusting a voltage applied to the varifocal lens without moving the mechanical position of the objective lens 4 along the optical axis. Thus, the mechanical lens movement mechanism as described in FIG. 1 can be omitted.

By the use of the varifocal lens also as the lens 5 that condenses the reflected light, by adjusting the voltage applied to the varifocal lenses in order to move the focal positions of the objective lens 4 and the lens 5 and a position of the pin hole 6 in a synchronized way, the positions can be controlled such that a focused measurement position in the living body LB and the pin hole position are optically conjugate to each other.

Figure 3:
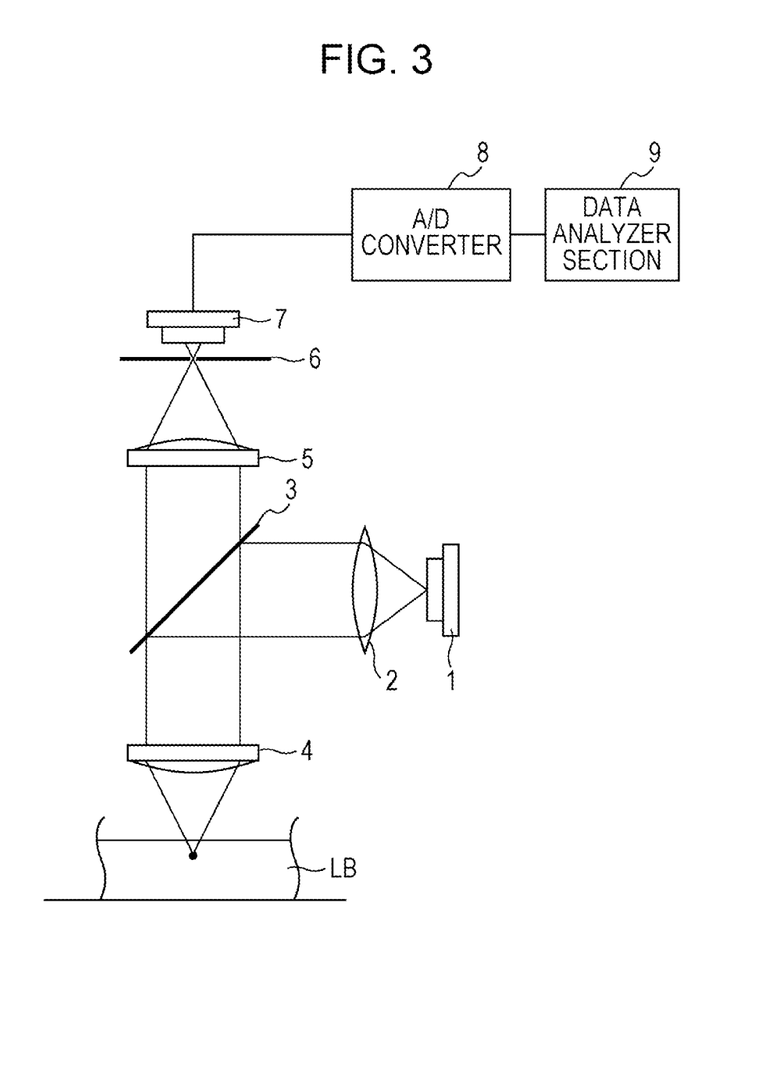
FIG. 3 is a block diagram illustrating yet another embodiment according to the present disclosure.

FIG. 3 is a block diagram illustrating yet another embodiment according to the present disclosure. In the embodiment illustrated in FIG. 3, the light receiver system including the pin hole 6 and the light-receiving element 7 is disposed so as to oppose the living body LB, and the laser diode 1 is disposed in a direction perpendicular to the optical axis of the light receiver system. By doing this, component measurement similar to that performed with the apparatus in FIG. 2 can be performed.

Figure 4:
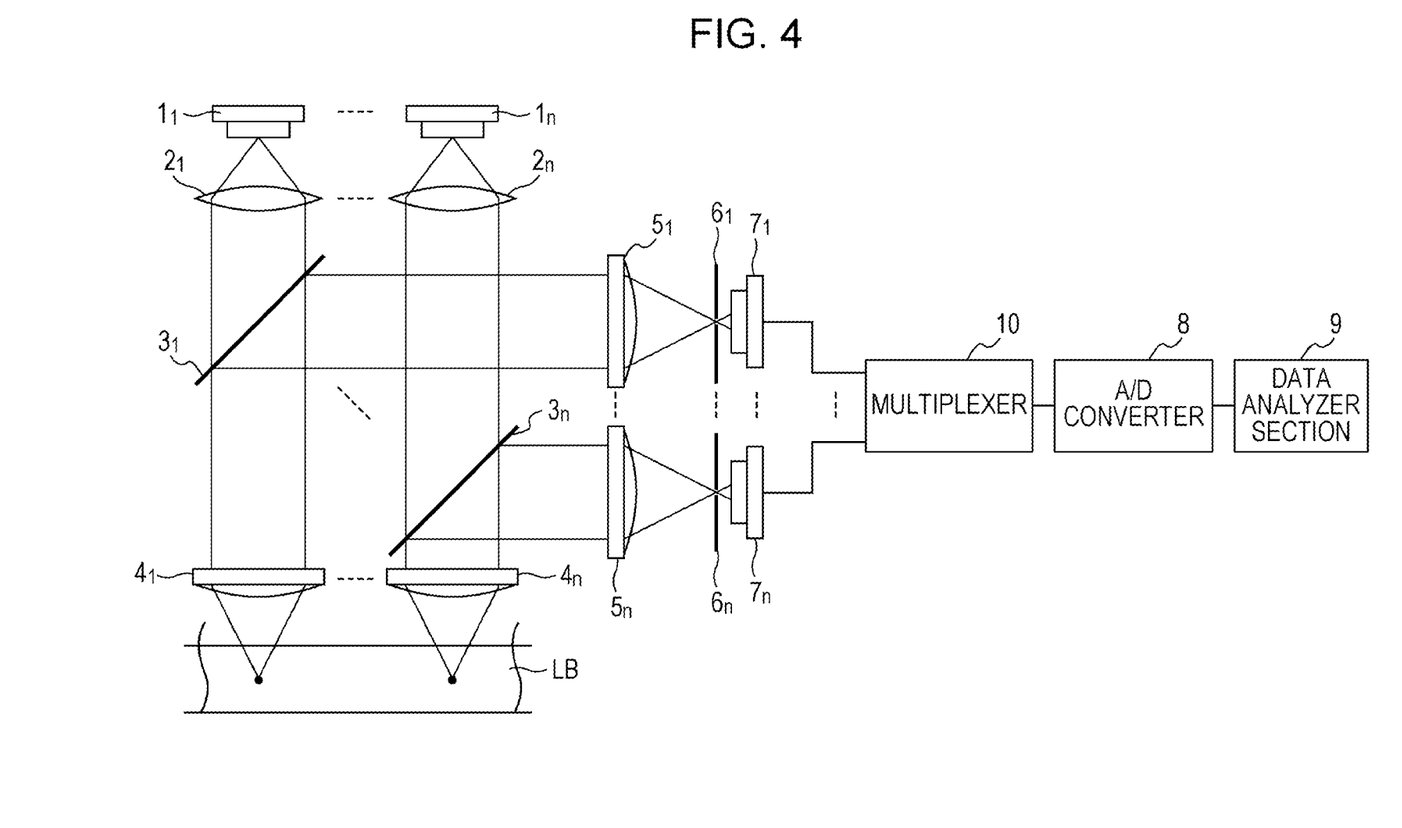
FIG. 4 is a block diagram illustrating yet another embodiment according to the present disclosure.

FIG. 4 is a block diagram illustrating yet another embodiment according to the present disclosure. In the embodiment illustrated in FIG. 4, the component measurement apparatus structured as illustrated in FIG. 2 is unitized, and a plurality of such units, that is, n units, are integrated in an array. By arranging those measurement units into the array, signals of different focal positions in the living body LB and of different wavelengths can be collectively obtained. Output signals from the individual light-receiving elements 7 are sent to the common A/D converter 8 through a multiplexer 10 and converted into digital data. However, when processing at higher speed is required, each light-receiving element can be provided with a dedicated A/D converter.

In each of the above-described embodiments, by driving the laser diode 1 by an automatic output control loop so as to maintain the intensity of light emitted from the laser diode 1 toward the object of measurement at a certain value, stable measurement can be performed.

Figure 5:
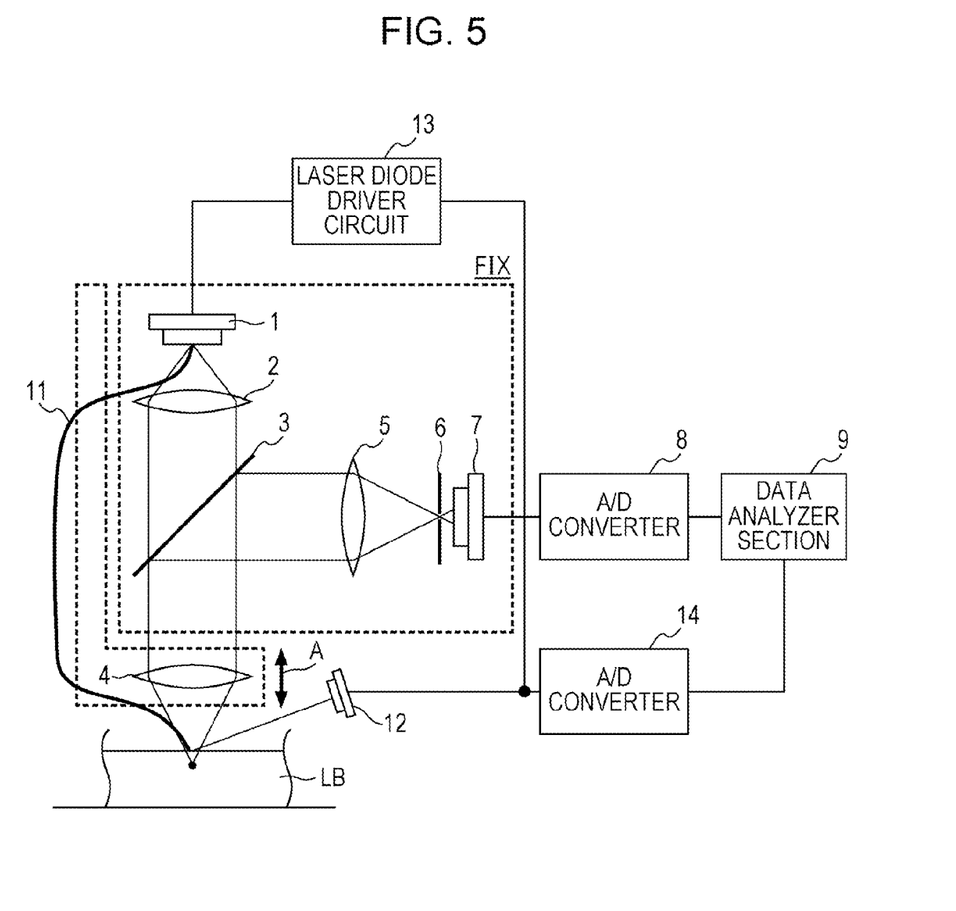
FIG. 5 is a block diagram illustrating yet another embodiment according to the present disclosure.

FIG. 5 is a block diagram illustrating an example in which the above-described structure is applied to the embodiment illustrated in FIG. 1. In the embodiment illustrated in FIG. 5, a surface of the living body LB as the object of measurement is illuminated with part of output light emitted from the laser diode 1 through an optical fiber 11. The light reflected by the surface of the living body LB is detected by a second light-receiving element 12. An output signal of this second light-receiving element 12 is sent to a laser diode driver circuit 13 in order to drive the laser diode 1 so as to maintain the output light intensity of the laser diode 1 at a certain value.

By doing this, changes in the output light intensity caused by temperature changes and spatial intensity variations of the laser diode 1 can be suppressed and a stable component measurement result can be obtained.

The output signal of the second light-receiving element 12 is also sent to the data analyzer section 9 through an A/D converter 14, and the output signal of the first light-receiving element 7 is divided by the output signal of the second light-receiving element 12 in order to be normalized. By doing this, output fluctuations of the laser diode 1 and variations due to reflection at the surface of the living body LB can be compensated for.

Figure 6:
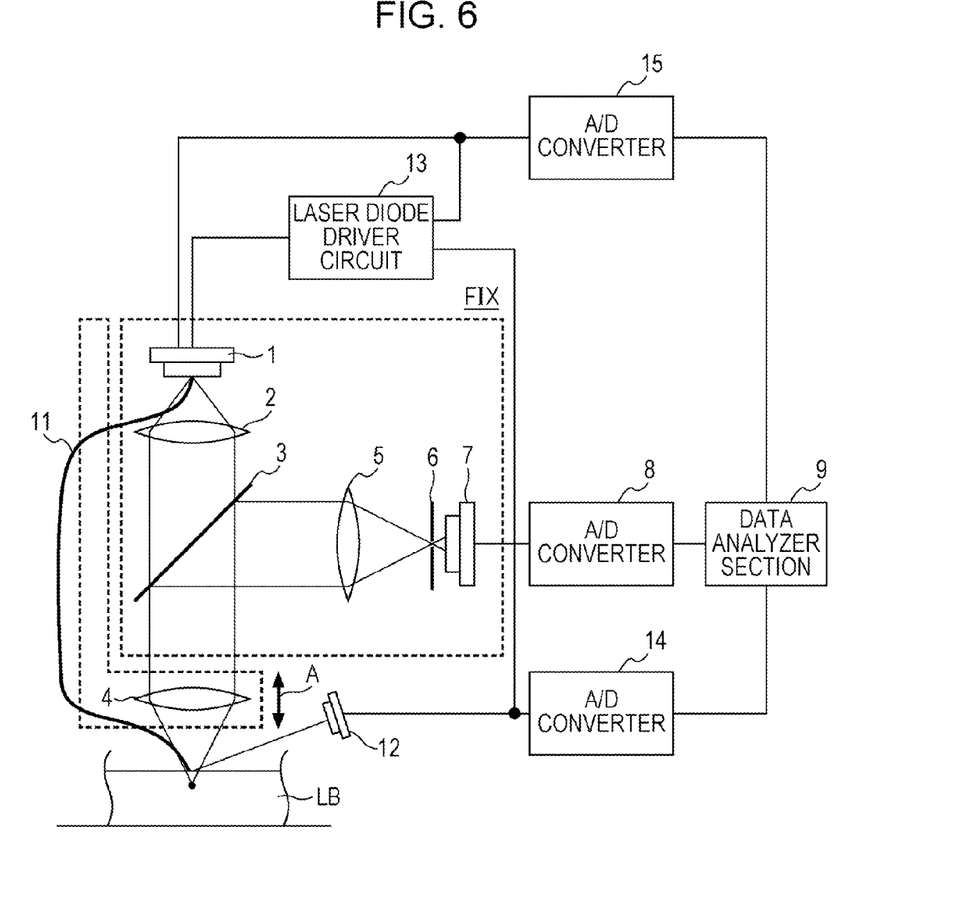
FIG. 6 is a block diagram illustrating yet another embodiment according to the present disclosure.

FIG. 6 is a block diagram illustrating an embodiment, in which the laser diode 1 illustrated in FIG. 5 includes a third light-receiving element (not shown) therein that monitors the output light thereof. An output signal of the third light-receiving element is also sent to the laser diode driver circuit 13 in order to drive the laser diode 1 so as to maintain the output light intensity of the laser diode 1 at a certain value.

The output signal of the third light-receiving element is also sent to the data analyzer section 9 through an A/D converter 15, and the output signal of the first light-receiving element 7 are divided by the output signal of the third light-receiving element in order to be normalized. By doing this, in the data analyzer section 9, the two normalized signals are linearly combined and a coupling factor is determined by a multivariate analysis. In accordance with these values, output fluctuations of the laser diode 1 and variations due to reflection at the surface of the living body LB are compensated for with a high degree of accuracy.

Figure 7:
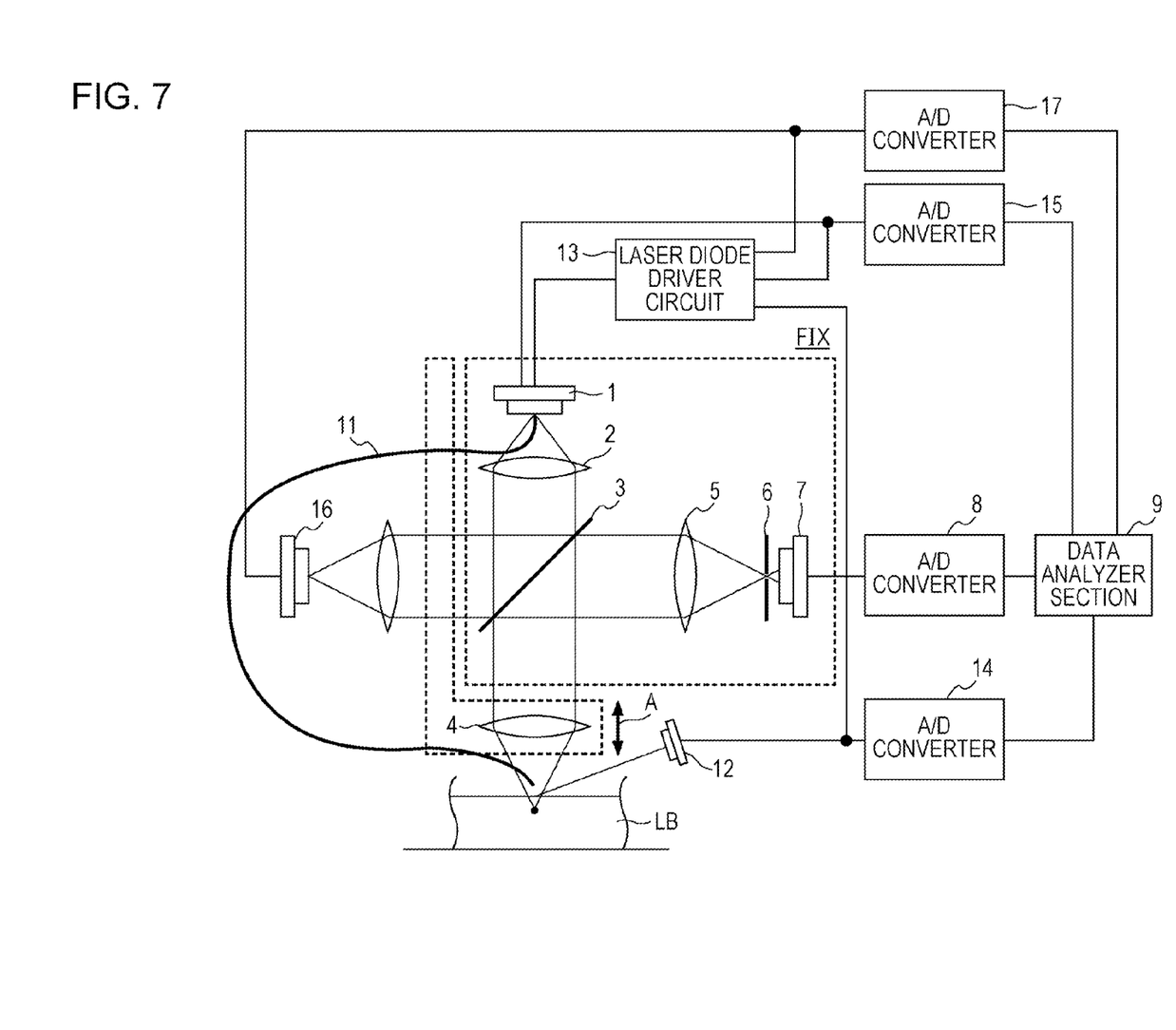
FIG. 7 is a block diagram illustrating yet another embodiment according to the present disclosure.

Referring to FIG. 7, a fourth light-receiving element 16, which detects the reflected light reflected by the half mirror 3, and an A/D converter 17, which converts an output signal of this fourth light-receiving element 16 into a digital signal, are further added to the embodiment illustrated in FIG. 6. The fourth light-receiving element 16 detects a spatial fluctuations of output light emitted from the laser diode 1. An output signal of the fourth light-receiving element 16 is also sent to the laser diode driver circuit 13 in order to drive the laser diode 1 so as to maintain the output light intensity of the laser diode 1 at a certain value.

The output signal of the fourth light-receiving element 16 is also sent to the data analyzer section 9 through the A/D converter 17, and the output signal of the first light-receiving element 7 is divided by the output signal of the fourth light-receiving element 16 in order to be normalized. By doing this, in the data analyzer section 9, the three normalized signals are linearly combined and a coupling factor is determined by a multivariate analysis. In accordance with these values, spatial variations and output fluctuations of the laser diode 1 and variations due to reflection at the surface of the living body LB are compensated for with a higher degree of accuracy.

Figure 8:
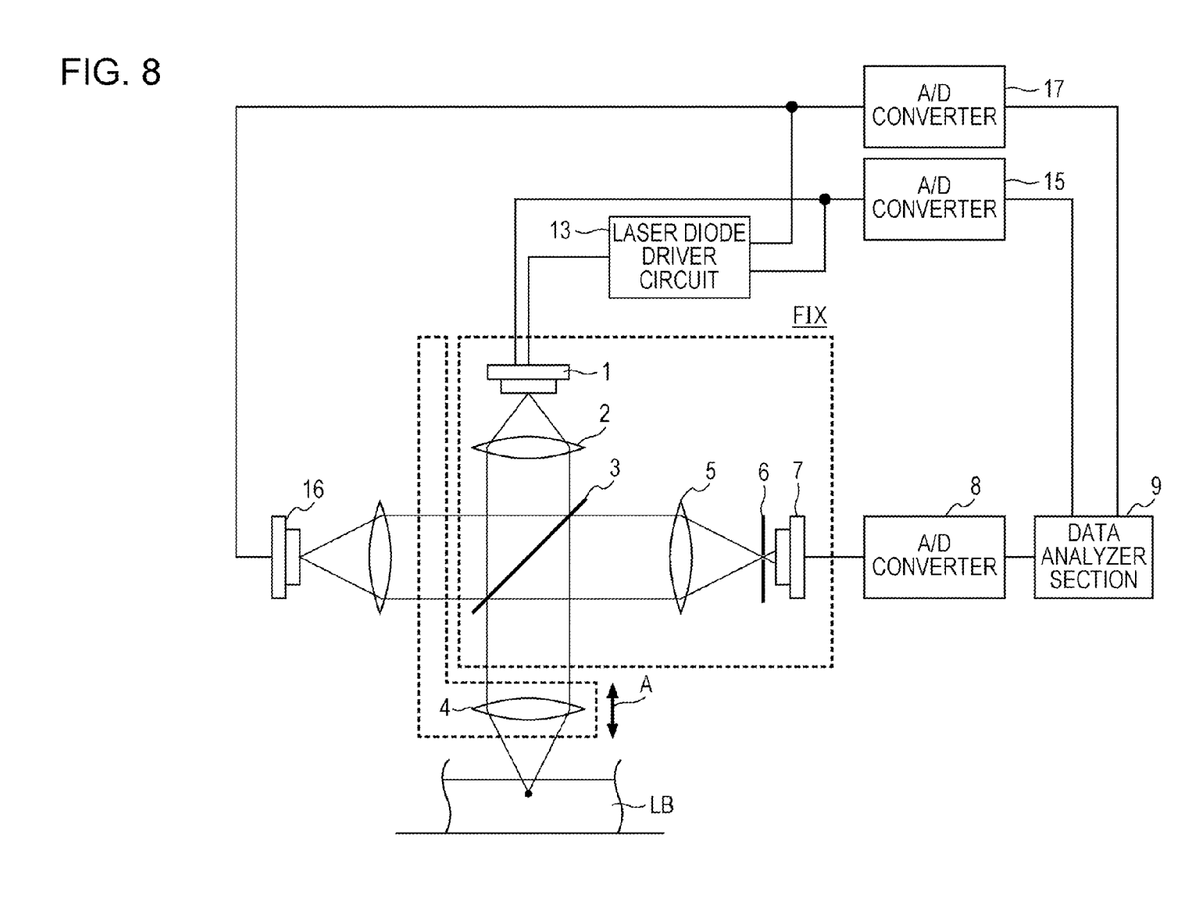
FIG. 8 is a block diagram illustrating yet another embodiment according to the present disclosure.

Referring to FIG. 8, a signal system including the optical fiber 11, the second light-receiving element 12, and the A/D converter 14 of the embodiment illustrated in FIG. 7 has been omitted. According to a structure illustrated in FIG. 8, the laser diode driver circuit 13 drives the laser diode 1 in accordance with the output signals of the third light-receiving element and the fourth light-receiving element 16 so as to maintain the output light intensity of the laser diode 1 at a certain value. With the data analyzer section 9, spatial variations and output fluctuations of the laser diode 1 can be compensated for with a high degree of accuracy in accordance with a normalized signal obtained by dividing the output signal of the first light-receiving element 7 by the output signal of the third light-receiving element and another normalized signal obtained by dividing the output signal of the first light-receiving element 7 by the output signal of the fourth light-receiving element 16.

The laser diode 1 used in each of the embodiments illustrated in FIGS. 7 and 8 includes the third light-receiving element therein that monitors the output light thereof. However, the laser diode 1 that does not include the third light-receiving element as illustrated in FIG. 5 may be used depending on compensation accuracy required by the apparatus.

Although the structures illustrated in FIGS. 5 to 8 may be applicable not only to the embodiment illustrated in FIG. 1, but also to the embodiments illustrated in FIGS. 2 to 4, block diagrams illustrating applications of the structures to these embodiments are omitted.

In each of the above-described embodiments, an example is described, in which a variable wavelength laser is used as the light source. However, the light source may be a single wavelength laser when a target component is specified.

Also, in each of the above-described embodiments, by incorporating a mechanism that moves a component measurement apparatus including the illumination and the light receiver systems and the living body LB relatively to each other in the X and Y directions, three-dimensional information in the living body LB can be obtained.

In each of the above-described embodiments, an example in which a blood glucose level in human blood is measured is described. However, the above-described examples are useful in quantitative measurement of a blood component and a tissue fluid component in addition to the measurement of a blood glucose level.

Also, an object of measurement is not limited to a human body. The apparatus is useful in quantitative measurement of an internal substance of an animal or a plant.

Furthermore, an object of measurement is not limited to a living body. The apparatus is also useful in non-destructive inspection of the structure and the composition of an agricultural product, a fishery product, food, an organic material, and so forth and in quantitative measurement of a chemical substance.

As described above, according to the present disclosure, the component measurement apparatus can be achieved, with which measurement data from a desired measurement position along the depth direction of the object of measurement can be adequately obtained. Thus, the component measurement apparatus according to the present disclosure is suitable for measurement of a variety of components including glucose level in human blood.

What is claimed is:

1. A component measurement apparatus, comprising:
   a confocal optical system that includes
      a laser that emits laser light,
      a collimating lens that shapes the laser light emitted from the laser into collimated light,
      an objective lens that condenses the collimated light having exited the collimating lens in order to illuminate internal tissue of an object of measurement,
      a half mirror that redirects reflected light reflected by the internal tissue of the object of measurement and refracted by the objective lens,
      a pin hole through which the reflected light redirected by the half mirror passes, and
      a first light-receiving element that receives the reflected light having passed through the pin hole;
   a data analyzer section that measures a component of the object of measurement in accordance with data output from the light-receiving element;
   an optical fiber used to illuminate a surface of the object of measurement with the output light of the laser;
   a second light-receiving element that detects reflected light reflected by the surface of the object of measurement due to illumination using the optical fiber; and
   a laser driver circuit that drives the laser so as to maintain an output light intensity of the laser at a certain value in accordance with detection signal of the second light-receiving element,
   wherein the objective lens is a varifocal lens having a focal position that is adjustable in an optical axis direction.

2. The component measurement apparatus according to claim 1,
   wherein the data analyzer section measures the component of the object of measurement in accordance with normalized data obtained by dividing a detection signal of the second light-receiving element that detects the reflected light reflected by the internal tissue of the object of measurement through the confocal optical system by the detection signal of the second light-receiving element.

3. The component measurement apparatus according to claim 1,
   wherein the laser includes a third light-receiving element therein that monitors the output light thereof, and
   wherein the laser driver circuit drives the laser in accordance with at least one of the detection signal of the second light-receiving element and a detection signal of the third light-receiving element so as to maintain the output light intensity of the laser at a certain value.

4. The component measurement apparatus according to claim 3, further comprising:
   a fourth light-receiving element that detects the reflected light reflected by the half mirror that is provided in an optical path of the laser light,
   wherein the laser driver circuit drives the laser in accordance with at least one of the detection signal of the second light-receiving element, the detection signal of the third light-receiving element, and a detection signal of the fourth light-receiving element so as to maintain the output light intensity of the laser at a certain value.

5. The component measurement apparatus according to claim 4,
   wherein the data analyzer section measures the component of the object of measurement in accordance with normalized data obtained by dividing the detection signal of the second light-receiving element that detects the reflected light reflected by the internal tissue of the object of measurement through the confocal optical system by at least one of the detection signal of the second light-receiving element, the detection signal of the third light-receiving element, the detection signal of the fourth light-receiving element.

6. The component measurement apparatus according to claim 4,
   wherein the data analyzer section measures the component of the object of measurement in accordance with data obtained by linear combination of normalized signals obtained by dividing the detection signal of the light-receiving element that detects the reflected light reflected by the internal tissue of the object of measurement through the confocal optical system by each of the detection signals of the second, third, and fourth light-receiving elements.

7. The component measurement apparatus according to claim 1,
wherein the laser includes a third light-receiving element therein that monitors the output light thereof, and
wherein the data analyzer section measures the component of the object of measurement in accordance with normalized data obtained by dividing a detection signal of the second light-receiving element that detects the reflected light reflected by the internal tissue of the object of measurement through the confocal optical system by at least one of the detection signal of the second light-receiving element and a detection signal of the third light-receiving element.

8. The component measurement apparatus according to claim 1,
wherein the laser includes a third light-receiving element therein that monitors the output light thereof, and
wherein the data analyzer section measures the component of the object of measurement in accordance with data obtained by linear combination of a first normalized signal and a second normalized signal, the first normalized signal being obtained by dividing a detection signal of the second light-receiving element that detects the reflected light reflected by the internal tissue of the object of measurement through the confocal optical system by the detection signal of the second light-receiving element, the second normalized signal being obtained by dividing the detection signal of the second light-receiving element that detects the reflected light reflected by the internal tissue of the object of measurement through the confocal optical system by a detection signal of the third light-receiving element.

9. A component measurement apparatus, comprising:
a confocal optical system that includes
a laser that emits a variable wavelength laser light,
a collimating lens that shapes the laser light emitted from the laser into collimated light,
an objective lens that condenses the collimated light having exited the collimating lens in order to illuminate internal tissue of an object of measurement,
a half mirror that redirects reflected light reflected by the internal tissue of the object of measurement and refracted by the objective lens,
a pin hole through which the reflected light redirected by the half mirror passes, and
a first light-receiving element that receives the reflected light having passed through the pin hole;
a data analyzer section that measures a component of the object of measurement in accordance with data output from the light-receiving element;
an optical fiber used to illuminate a surface of the object of measurement with the output light of the laser;
a second light-receiving element that detects reflected light reflected by the surface of the object of measurement due to illumination using the optical fiber; and
a laser driver circuit that drives the laser so as to maintain an output light intensity of the laser at a certain value in accordance with detection signal of the second light-receiving element,
wherein the objective lens is a varifocal lens having a focal position that is adjustable in an optical axis direction.

10. A component measurement apparatus according, comprising:
a confocal optical system that includes
a laser that emits laser light,
a collimating lens that shapes the laser light emitted from the laser into collimated light,
an objective lens that condenses the collimated light having exited the collimating lens in order to illuminate internal tissue of an object of measurement,
a half mirror that redirects reflected light reflected by the internal tissue of the object of measurement and refracted by the objective lens,
a pin hole through which the reflected light redirected by the half mirror passes, and
a first light-receiving element that receives the reflected light having passed through the pin hole;
a data analyzer section that measures a component of the object of measurement in accordance with data output from the light-receiving element;
an optical fiber used to illuminate a surface of the object of measurement with the output light of the laser;
a second light-receiving element that detects reflected light reflected by the surface of the object of measurement due to illumination using the optical fiber;
a laser driver circuit that drives the laser so as to maintain an output light intensity of the laser at a certain value in accordance with detection signal of the second light-receiving element; and
a movement mechanism that moves the confocal optical system and the object of measurement relatively to each other in three dimensions,
wherein the objective lens is a varifocal lens having a focal position that is adjustable in an optical axis direction.

11. A component measurement apparatus, comprising:
a confocal optical system that includes
a laser that emits laser light,
a collimating lens that shapes the laser light emitted from the laser into collimated light,
an objective lens that condenses the collimated light having exited the collimating lens in order to illuminate internal tissue of an object of measurement,
a half mirror that redirects reflected light reflected by the internal tissue of the object of measurement and refracted by the objective lens,
a pin hole through which the reflected light redirected by the half mirror passes, and
a first light-receiving element that receives the reflected light having passed through the pin hole;
a data analyzer section that measures a component of the object of measurement in accordance with data output from the light-receiving element;
an optical fiber used to illuminate a surface of the object of measurement with the output light of the laser;
a second light-receiving element that detects reflected light reflected by the surface of the object of measurement due to illumination using the optical fiber; and
a laser driver circuit that drives the laser so as to maintain an output light intensity of the laser at a certain value in accordance with detection signal of the second light-receiving element,
wherein the objective lens is a varifocal lens having a focal position that is adjustable in an optical axis direction,
wherein the component of the object of measurement is glucose in blood, and wherein the data analyzer section quantitatively determines a concentration of the glucose by measuring absorbance of the glucose in the internal tissue of the object of measurement in accordance with the data output from the light-receiving element and determines a blood glucose level.

* * * * *